United States Patent [19]

Reswick et al.

[11] 4,158,895

[45] Jun. 26, 1979

[54] PROSTHESIS COUPLING

[76] Inventors: Robert A. Frosch, Adminstrator of the National Aeronautics and Space Administration, with respect to an invention of James B. Reswick; Vert Mooney, both of Downey, Calif.; Charles W. Bright; Lester J. Owens, both of Titusville, Fla.

[21] Appl. No.: 876,438

[22] Filed: Feb. 9, 1978

[51] Int. Cl.² .............................. A61F 1/06; A61F 1/08
[52] U.S. Cl. .................................................. 3/2; 3/1.9; 3/12
[58] Field of Search .............................. 3/1, 1.9–1.912, 3/2, 12, 12.1

[56] References Cited
U.S. PATENT DOCUMENTS

| | | | |
|---|---|---|---|
| 3,938,198 | 2/1976 | Kahn et al. | 3/1.912 |
| 3,947,897 | 4/1976 | Owens | 3/2 |

OTHER PUBLICATIONS

"A Permanently Attached Artificial Limb", by C. W. Hall et al., Transactions Amer. Society Artificial Internal Organs, vol. XIII, 1967, pp. 329–331.

Primary Examiner—Ronald L. Frinks
Attorney, Agent, or Firm—James O. Harrell; John R. Manning

[57] ABSTRACT

A coupling for use in an apparatus for connecting a prosthesis to the bone of a stump of an amputated limb which permits a bio-compatible carbon sleeve forming a part of the prosthesis connector to float so as to prevent disturbing the skin seal around the carbon sleeve. The coupling includes a flexible member interposed between a socket that is inserted within an intermedullary cavity of the bone and the sleeve. A lock pin is carried by the prosthesis and has a stem portion which is adapted to be coaxially disposed and slideably within the tubular female socket for securing the prosthesis to the stump. The skin around the percutaneous carbon sleeve is able to move as a result of the flexing coupling so as to reduce stresses caused by changes in the stump shape and/or movement between the bone and the flesh portion of the stump.

6 Claims, 3 Drawing Figures

PROSTHESIS COUPLING

ORIGIN OF THE INVENTION

The invention described herein was made in performance in work under a NASA Contract and is subject to the provisions of Section 305 of National Aeronautics and Space Act of 1968, Public Law 85-568 (72 Stat. 435, 402 USCP. 2457).

BACKGROUND OF THE INVENTION

The present invention relates to a coupling device for a prosthesis, and more particularly to a flexible coupling that floats relative to the bone of an amputated limb so as to minimize disturbing the skin seal around the sleeve forming part of the socket.

Artificial limbs, or prothesis, have been used by amputees for many centuries. At first the prothesis were crude, shaped as sticks attached to legs or as hooks attached to arms. Recently, they have become more sophisticated, incorporating electronic equipment and servo motors to produce more natural limb movement. With all this development, however, problems still remain in means of attaching the prosthesis. When porothesis are worn for a long time, the harness and clamps create discomforting pressures.

Attempts have been made to minimize these problems, and one example such an attempt is disclosed in U.S. Pat. No. 3,947,897. In that particular device, a quick disconnecting lock pin is attached to the prosthesis and a socket is inserted within the intermedullary cavity of the bone for receiving such a pin. Interposed between the end of the socket and the skin is a sleeve constructed of bio-compatible material which provides compatibility between the implanted socket and the skin line which, in turn, heals therearound.

One problem with such a device is that the sleeve is fixed relative to the socket and stresses that are produced as a result of changes in the stump shape tend to cause the skin seal around the carbon sleeve to be disturbed.

SUMMARY OF THE INVENTION

The invention includes a coupling for use in apparatus for connecting a prosthesis to a bone of a stump of an amputated limb. The apparatus includes a tubular female socket having an open lower end adapted to be inserted within the intermedullary cavity of the bone. A bio-compatible sleeve provides an interface between the female socket and the skin directly below the opening in the socket. A lock pin is carried by the prosthesis and has a stem portion adapted to be coaxially disposed and slideably within the tubular female socket for securing the prosthesis to the stump. The coupling is constructed of resilient material with one end thereof being attached to the socket and the other end thereof being attached by any suitable material to the bio-compatible sleeve. In one particular embodiment the resilient member has a bulbous portion which aids in maintaining the sleeve and the socket separated for providing a flexible connection therebetween. In another embodiment, the flexible material extends radially outwardly from a lower end of the socket and is attached to both the socket and the bio-compatible sleeve. A reinforcing mesh pleated material may be implanted in the resilient member for allowing lateral movement therein.

Accordingly it is an important object of the present invention to provide a coupling device for use in a connector so as to permit movement between a bio-compatible sleeve and a socket forming part of a connector for securing a prosthesis to an amputated limb.

Another important object of the present invention is to provide a simple and relatively inexpensive coupling for securing a bio-compatible sleeve forming part of a prosthesis connector so as to permit the sleeve to float relative to the socket.

Still another important object of the present invention is to provide a resilient coupling for a prosthesis which minimizes disturbing the skin seal around a bio-compatible carbon sleeve as a result of changes in shape of a stump of an amputated limb, or having the skin and flesh pulled or pushed relative to the bone.

These and other objects and advantages of the invention will become apparent upon reference to the following specification, attendant claims and drawings.

DESCRIPTION OF A PREFERRED EMBODIMENT

Figure 1:
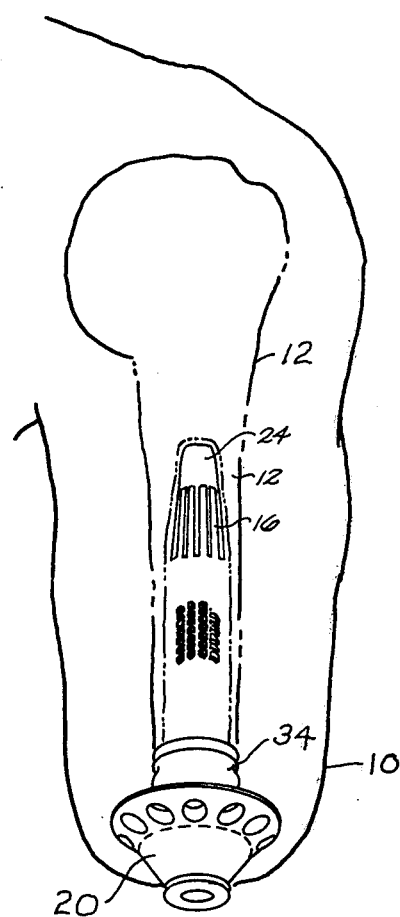
FIG. 1 is a perspective view illustrating an apparatus for connecting a prosthesis to a bone of a stump of an amputated limb.

Referring in more detail to FIG. 1 of the drawing, there is illustrated a stump 10 of an amputated limb, such as the upper arm showing the bone 12 remaining in the stump. Marrow carried in the lower end of the medullary canal is removed so as to accommodate a tubular female socket 16 which is constructed of any suitable material such as stainless steel. The socket 16 is inserted within the medullary canal into the lower end of the bone 12 which has been previously trimmed so that the bone 12 abuts against an outwardly extending shoulder 18 carried adjacent the lower end of the socket 16. A sleeve 20 of bio-compatible material is carried below the female socket so as to provide a compatible interface between the implanted socket 16 and the skin line 22 which heals therearound. One suitable material that is compatible with the flesh and skin of the body is vitreous carbon.

The tubular female socket 16 is secured to the inner surface of the bone 12 by means of any suitable bonding material, such as methylmethacrylate. Normally, the outer surface of the sleeve is grooved or knurled so as to enable the bonding material to produce a good interface bond between the bone 12 and the socket 16. In order to minimize the stress between the socket 16 and the bone 12 the upper end of the socket such as at 24, tapers inwardly. The purpose of this inwardly tapering surface 24 adjacent the top of the socket 16 is to minimize stress concentration that may be incurred when the prosthesis is attached thereto. This inwardly tapering surface 24 may be curved slightly to form a portion of a three-dimensional ogive to match the curvature of the inner surface of the bone under maximum bending. This ogive also assists in ease of inserting the socket into the bonding material within the medullary canal.

The tubular sleeve 16 has an internal annular groove 26 provided for receiving balls 28 carried within a lock pin 30 for securing a prosthesis generally designated by the reference character 32 to the stump 10. There may be multiple grooves to eliminate need of socket removal should the primary groove become unsuitable through wear or damage.

The prosthesis may be constructed of any suitable conventional material and may be attached to the locking pin 30 in any suitable manner such as disclosed in greater detail in U.S. Pat. No. 3,947,897.

Interposed between the lower end of the socket 16 and the bio-compatible sleeve 20 is a resilient coupling member 34. The resilient member 34 has an upper portion that is attached by any suitable bonding agent to the lower end of the socket and to the bottom side of the shoulder 18. The lower end 36 of the resilient member extends into the tubular opening provided in the sleeve 20 and is secured to a stainless steel sleeve 40 which, in turn, is secured to the inner surface of the sleeve 20 by any suitable means, such as a bio-compatible bonding agent. Ridges may also be provided in the inner surface of the sleeve 40 for aiding in securing the resilient member thereto.

The resilient member 34 includes a bulbous portion 38 which separates the lower end of the socket 16 from the sleeve 20 while providing a flexible connection therebetween. The flexible coupling 34 may be constructed of any suitable material such as bio-compatible polyurethane or silicone rubber. In one particular application the flexible member 34 is constructed of RTV silicone manufactured by Dow Corning Company and is identified as MDX4-4210.

After the socket has been implanted into the stump, the skin grows up around the bio-compatible carbon sleeve 20 and provides a skin seal therebetween. It is important that this seal not be disturbed, however, it has been found in the past that as a result of changes in stump shape, stresses occur which often break the seal between the skin and the bio-compatible sleeve 20. The flexible coupling 34 permits the sleeve to more or less float relative to the socket 16 to compensate for changes in the shape of the stump. As a result, the chance of the skin seal provided between the skin line 22 and the bio-compatible sleeve 20 being disturbed is minimized.

It is to be understood of course, that while the prosthesis is shown coupled to an upper arm, the same coupling could be used on other limbs such as the lower leg.

Figure 2:
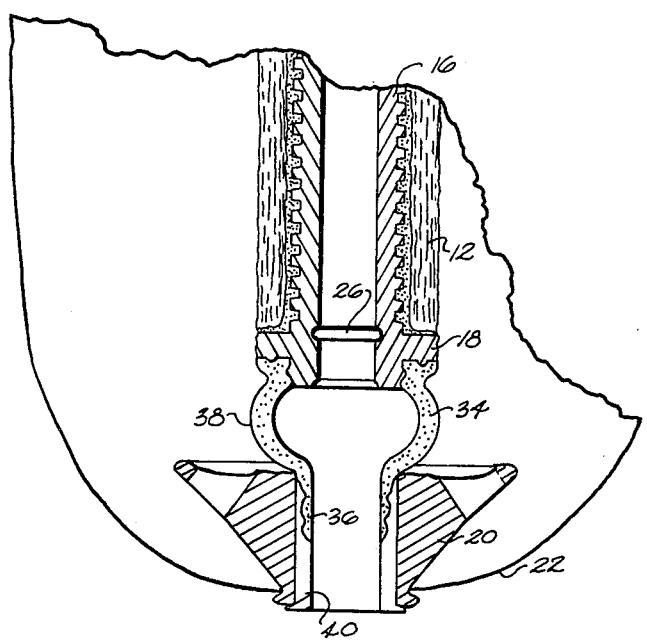
FIG. 2 is an enlarged fragmentary cross-sectional view of the connector illustrated in FIG. 1.
Figure 3:
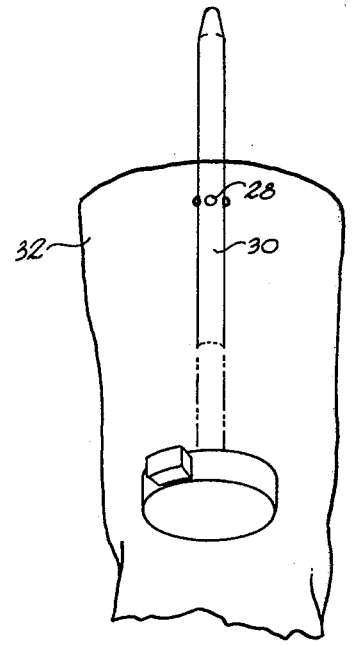
FIG. 3 is an enlarged sectional view of a modified form of the invention.

Referring now to FIG. 3 of the drawing, there is illustrated a modified form of the invention. Like reference numerals are utilized for like and corresponding parts similar to that of FIGS. 1 and 2. In the embodiment illustrated in FIG. 3, a different shape bio-compatible sleeve 42 is utilized. In this particular embodiment the bio-compatible sleeve 42 is concentric to the lower end of the socket 16 and has a much larger bore extending therethrough. A stainless steel sleeve 44 is secured to the lower portion of the inner wall of the sleeve 42 for adding strength thereto. A resilient member 46 has its inner end attached to the socket by means of any suitable bonding agent. The resilient member 46 has a portion 48 extending radially outwardly from the socket and is secured to the inner wall 50 of the bio-compatible sleeve 42 by any suitable means. A concentrically pleated reinforcing member 52 can be implanted in the radially extended portion 48 so as to allow lateral movement of the resilient member.

While a preferred embodiment of the invention has been described using specific terms, such description is for illustrative purposes only, and it is to be understood that changes and variations may be made without departing from the spirit or scope of the following claims.

What is claimed is:

1. A coupling for use in an apparatus for connecting a prosthesis to a bone of a stump of an amputated limb, said apparatus including a tubular female socket having an open lower end adapted to be inserted within an intermedullary cavity of the bone, a sleeve for providing an interface between said female socket and the skin directly below the opening in said socket, and a lock pin carried by said prosthesis having a stem portion adapted to be coaxially disposed and slideably within said tubular female socket for securing said prosthesis to said stump, said coupling comprising:
   (a) a resilient member interposed between said tubular female socket and said sleeve;
   (b) means for attaching an inner portion of said resilient member to a lower end of said socket;
   (c) means for attaching an outer portion of said resilient member to said sleeve; and
   (d) said resilient member having an intermediate flexible portion permitting said sleeve to move relative to said socket;
   whereby disturbing of the skin seal between said sleeve and said skin is minimized by permitting said sleeve to move relative to said socket.

2. The coupling as set forth in claim 1 wherein said resilient member comprises:
   a tubular member constructed of resilient material;
   one end of said tubular member being attached to said socket; and
   the other end of said tubular member being connected to said sleeve.

3. The coupling as set forth in claim 2 wherein said intermediate flexible portions comprises:
   a bulbous portion maintaining said sleeve and said socket separated while providing a fixable connection therebetween.

4. The coupling as set forth in claim 1 further comprising:
   a pleated reinforcing element carried in said intermediate flexible portion.

5. The coupling as set forth in claim 1 further comprising:
   said sleeve being concentrically disposed relative to a lower end of said socket; and
   said resilient member extending radially outwardly from said lower end of said socket resiliently connecting said sleeve to said socket.

6. An apparatus for connecting a prosthesis to a bone of a stump of an amputated limb comprising:
   (a) a tubular female socket adapted to be inserted within an intermedullary cavity of the bone;
   (b) a bio-compatible sleeve adapted to be carried adjacent the skin line of the stump so that the skin can heal therearound providing a skin seal;
   (c) a resilient member connected between said bio-compatible sleeve and said tubular female socket providing a resilient connection therebetween so as to permit shifting of said bio-compatible sleeve relative to said socket; and
   (d) a lock pin carried by said prosthesis having a stem portion adapted to be coaxially disposed and slideably within said tubular female socket for securing said prosthesis to said stump.

* * * * *